US010449223B2

(12) United States Patent
Kuo et al.

(10) Patent No.: US 10,449,223 B2
(45) Date of Patent: Oct. 22, 2019

(54) **USE OF DEHYDROEBURICOIC ACID FROM *ANTRODIA CAMPHORATA* IN THE TREATMENT OR PREVENTION OF DIABETES AND HYPERLIPIDEMIA**

(71) Applicant: Chung-Ching Shih, Taichung (TW)

(72) Inventors: Yueh-Hsiung Kuo, Taipei (TW); Cheng-Hsiu Lin, Taichung (TW); Chun-Ching Shih, Taichung (TW)

(73) Assignee: Chun-Ching Shih, Taichung (TW)

( * ) Notice: Subject to any disclaimer, the term of this patent is extended or adjusted under 35 U.S.C. 154(b) by 0 days.

(21) Appl. No.: 15/229,075

(22) Filed: Aug. 4, 2016

(65) Prior Publication Data

US 2017/0216384 A1      Aug. 3, 2017

(30) Foreign Application Priority Data

Feb. 1, 2016   (TW) .............................. 105103079 A

(51) Int. Cl.
*A61K 36/07*   (2006.01)
*A61K 31/57*   (2006.01)
*A61K 31/575*  (2006.01)

(52) U.S. Cl.
CPC .............. *A61K 36/07* (2013.01); *A61K 31/57* (2013.01); *A61K 31/575* (2013.01)

(58) Field of Classification Search
CPC ...................................................... A61K 36/07
USPC ......................................................... 514/182
See application file for complete search history.

(56) References Cited

U.S. PATENT DOCUMENTS

2011/0053899 A1* 3/2011 Lin ...................... A61K 31/575
514/170

OTHER PUBLICATIONS

Huang, Food Chemistry 141 (2013) 3020-3027.*
Kuo et al. Journal of agricultural and food chemistry (2015), 63(46), 10140-51.*
Sato et al. Biological & Pharmaceutical Bulletin (2002), 25(1),81-86.*
Lien, et al Molecules (2014), 19(7), 9033-9050, 18 pp.*
Huang et al. Food Chemistry 141 (2013) 3020-3027.*
Planavila Biochemical Pharmacology (2005), 69(8), 1195-1204.*
Tai Planta Med. 61(1995)527-530 and Tai1 Phytochemistry (1995), 39(5), 1165-9.*
Tai1 Phytochemistry (1995), 39(5), 1165-9.*
Chou, Journal of Functional Foods (2013), 5(3), 1317-1325.*
Marriott, Pharmaceutical Compound and Dispensing, Second Edition, 2010, 1-288.*

* cited by examiner

*Primary Examiner* — Nizal S Chandrakumar
(74) *Attorney, Agent, or Firm* — Muncy, Geissler, Olds & Lowe, P.C.

(57) ABSTRACT

The present invention provides a method for treating type 1 diabetes, hyperlipidemia or hepatic lipid accumulation by using dehydroeburicoic acid, as well as a method for decreasing levels of blood glucose, plasma total cholesterol, and triglyceride, and increasing insulin levels; and a method for decreasing hepatic balloon degeneration; and increasing expression levels of membrane GLUT4 and phospho-Akt in myotubes; and enhancing expression levels of membrane glucose transporter 4 (GLUT4) in skeletal muscle, and phospho-AMPK in both skeletal muscle and liver tissue using dehydroeburicoic acid.

10 Claims, 10 Drawing Sheets

Specification includes a Sequence Listing.

SEQUENCE LISTING

```
<160> NUMBER OF SEQ ID NOS: 16

<210> SEQ ID NO 1
<211> LENGTH: 20
<212> TYPE: DNA
<213> ORGANISM: Artificial sequence
<220> FEATURE:
<223> OTHER INFORMATION: Synthesized Forward primer PEPCK Seq No.
      NM_011044.2

<400> SEQUENCE: 1
ctacaacttc ggcaaatacc                                              20

<210> SEQ ID NO 2
<211> LENGTH: 20
<212> TYPE: DNA
<213> ORGANISM: Artificial sequence
<220> FEATURE:
<223> OTHER INFORMATION: Synthesized Reverse primer PEPCK Seq No.
      NM_011044.2

<400> SEQUENCE: 2
tccagatacc tgtcgatctc                                              20

<210> SEQ ID NO 3
<211> LENGTH: 22
<212> TYPE: DNA
<213> ORGANISM: Artificial sequence
<220> FEATURE:
<223> OTHER INFORMATION: Synthesized Forward primer G6-Pase Seq No.
      NM_008061.3
```

```
<400> SEQUENCE: 3
gaacaactaa agcctctgaa ac                                              22

<210> SEQ ID NO 4
<211> LENGTH: 22
<212> TYPE: DNA
<213> ORGANISM: Artificial sequence
<220> FEATURE:
<223> OTHER INFORMATION: Synthesized Reverse primer G6-Pase Seq No.
      NM_008061.3

<400> SEQUENCE: 4
ttgctcgata cataaaacac tc                                              22

<210> SEQ ID NO 5
<211> LENGTH: 20
<212> TYPE: DNA
<213> ORGANISM: Artificial sequence
<220> FEATURE:
<223> OTHER INFORMATION: Synthesized Forward primer PPAR(alpha) Seq No.
      NM_011144

<400> SEQUENCE: 5
acctctgttc atgtcagacc                                                 20

<210> SEQ ID NO 6
<211> LENGTH: 20
<212> TYPE: DNA
<213> ORGANISM: Artificial sequence
<220> FEATURE:
<223> OTHER INFORMATION: Synthesized Reverse primer PPAR(alpha) Seq No.
      NM_011144

<400> SEQUENCE: 6
ataaccacag accaaccaag                                                 20

<210> SEQ ID NO 7
<211> LENGTH: 20
<212> TYPE: DNA
<213> ORGANISM: Artificial sequence
<220> FEATURE:
<223> OTHER INFORMATION: Synthesized Forward primer SREBP-1c Seq No.
      NM_011480

<400> SEQUENCE: 7
ggctgttgtc taccataagc                                                 20

<210> SEQ ID NO 8
<211> LENGTH: 20
<212> TYPE: DNA
<213> ORGANISM: Artificial sequence
<220> FEATURE:
<223> OTHER INFORMATION: Synthesized Reverse primer SREBP-1c Seq No.
      NM_011480

<400> SEQUENCE: 8
aggaagaaac gtgtcaagaa                                                 20

<210> SEQ ID NO 9
<211> LENGTH: 23
<212> TYPE: DNA
<213> ORGANISM: Artificial sequence
<220> FEATURE:
<223> OTHER INFORMATION: Synthesized Forward primer DGAT2 Seq No.
      NM_026384.3

<400> SEQUENCE: 9
```
agtggcaatg ctatcatcat cgt                                                    23

<210> SEQ ID NO 10
<211> LENGTH: 24
<212> TYPE: DNA
<213> ORGANISM: Artificial sequence
<220> FEATURE:
<223> OTHER INFORMATION: Synthesized Reverse primer DGAT2 Seq No.
      NM_026384.3

<400> SEQUENCE: 10
aaggaataag tgggaaccag atca                                                   24

<210> SEQ ID NO 11
<211> LENGTH: 20
<212> TYPE: DNA
<213> ORGANISM: Artificial sequence
<220> FEATURE:
<223> OTHER INFORMATION: Synthesized Forward primer CPT1a Seq No.
      NM_153679

<400> SEQUENCE: 11
gcaggaaatt tacctctgtg                                                        20

<210> SEQ ID NO 12
<211> LENGTH: 20
<212> TYPE: DNA
<213> ORGANISM: Artificial sequence
<220> FEATURE:
<223> OTHER INFORMATION: Synthesized Reverse primer CPT1a Seq No.
      NM_153679

<400> SEQUENCE: 12
acatgaaggg tgaagatgag                                                        20

<210> SEQ ID NO 13
<211> LENGTH: 20
<212> TYPE: DNA
<213> ORGANISM: Artificial sequence
<220> FEATURE:
<223> OTHER INFORMATION: Synthesized Forward primer SREBP-2 Seq No.
      AF289715.2

<400> SEQUENCE: 13
atatcattga aaagcgctac                                                        20

<210> SEQ ID NO 14
<211> LENGTH: 20
<212> TYPE: DNA
<213> ORGANISM: Artificial sequence
<220> FEATURE:
<223> OTHER INFORMATION: Synthesized Reverse primer SREBP-2 Seq No.
      AF289715.2

<400> SEQUENCE: 14
attttcaagt ccacatcact                                                        20

<210> SEQ ID NO 15
<211> LENGTH: 20
<212> TYPE: DNA
<213> ORGANISM: Artificial sequence
<220> FEATURE:
<223> OTHER INFORMATION: Synthesized Forward primer GAPDH Seq No.
      NM_008084.3

<400> SEQUENCE: 15

```
tgtgtccgtc gtggatctga                                              20

<210> SEQ ID NO 16
<211> LENGTH: 21
<212> TYPE: DNA
<213> ORGANISM: Artificial sequence
<220> FEATURE:
<223> OTHER INFORMATION: Synthesized Reverse primer GAPDH Seq No.
      NM_008084.3

<400> SEQUENCE: 16
cctgcttcac caccttcttg a                                            21
```

USE OF DEHYDROEBURICOIC ACID FROM *ANTRODIA CAMPHORATA* IN THE TREATMENT OR PREVENTION OF DIABETES AND HYPERLIPIDEMIA

BACKGROUND OF THE INVENTION

Field of the Invention

The present invention provides a method of suppressing of diabetes, hyperlipidemia, hypertriglyceridemia, and hypercholesterolemia. Specially, the invention relates to a method of suppressing type 1 diabetes mellitus, hyperlipidemia, or hepatic ballooning degeneration and increasing insulin levels with dehydroeburicoic acid (TT) obtained from mycelium of *Antrodia camphorata*. The mediated-mechanisms demonstrated that TT significantly enhanced the expressions of Akt-phosphorylation in myotubes and phosphorylation of AMP-activated protein kinase (phospho-AMPK) in both skeletal muscle and liver tissue and increased membrane glucose transporter 4 (GLUT4) in skeletal muscle.

Related Prior Art

Diabetes mellitus type 1 is a metabolic disorder characterized by chronic hyperglycemia, and the pathophysiology is a destruction of β-cells in the pancreas. Type 1 diabetes causes an estimated 5-10% of all diabetes cases and is associated with many complications, and those are considered the causes of morbidity and mortality in patients with diabetes. Treatment of type 1 diabetes focuses on lowering blood glucose to the near normal range to avoid long-term complications that affect the nervous and cardiovascular systems.

The major cellular mechanism that diminishes blood glucose when carbohydrates are ingested is insulin-stimulated glucose transport into skeletal muscle. The principal glucose transporter protein that mediates this uptake is glucose transporter 4 (GLUT4), which plays a key role in the regulation during blood glucose homeostasis. The major cellular mechanism for disposal of exogenous glucose load is insulin-stimulated glucose transport into skeletal muscle. GLUT4 is proposed to be a key determinant of glucose homeostasis. Insulin stimulates glucose uptake in skeletal muscle and adipose cells primarily by inducing net translocation of GLUT4 from the intracellular storage sites to the plasma membrane. Impairment of GLUT4 expression, GLUT4 translocation, and/or insulin signaling may affect insulin-stimulated glucose uptake and would result in insulin resistance and hyperglycemia. These highlight a potential role of the improvement of GLUT4 contents and/or translocation to the plasma membrane in the treatment of diabetes mellitus.

GLUT4 translocation is mainly regulated by two pathways: the insulin signaling pathway and the AMP-activated protein kinase (AMPK) pathway. AMPK is also proposed to regulate GLUT4 translocation. Since Activation of the AMPK results in increased lipid and glucose catabolism, AMPK is considered as a therapeutic target for the treatment of diabetes and dyslipidemia.

There are several methods employed to induce type 1 diabetes mellitus in the laboratory. Streptozotocin (STZ), a diabetogenic agent with pancreatic β-cell toxicity ability, is convenient and simple to use for producing chemically induced diabetes models when administered in a single large dose or in repeated low doses for several days. STZ is widely used in inducing experimental animal models with type 1 DM. The STZ-induced diabetic rodent model is usually characterized by fasting or non-fasting hyperglycemia and lowered serum insulin levels with hyperlipidemia; however, insulin resistance is often absent in these models. Due to this limitation, although these models cannot be considered as appropriate models for T2D, they can be used for the screening of antihyperglycemic or insulinotropic drugs and natural medicines.

*Antrodia camphorata* (Polyporaceae, Aphyllophorales) is a parasitic microorganism found on the wall of the inner cavity of *Cinnamomum kanehirai* Hay. The fruiting body and cultured mycelia contain fatty acids, lignans, phenyl derivatives, sesquiterpenes, steroids, and triterpenoids. A recent study has revealed that the fermented culture broth exhibited cytotoxic, anti-inflammation, and vasorelation activities. The solid culture of fruiting body and the filtrate in submerged culture showed protective activity against CCl4-induced hepatic toxicity and antioxidant property. Dehydroeburicoic acid (TT) (FIG. 1) has been isolated from *Poria cocos* and *Antrodia camphorata* (*A. camphorata*). However, the antidiabetic and antihyperlipidemic effects of TT from the mycelia of *A. camphorata* are not well-defined in STZ induced diabetic mice.

SUMMARY

The first object of the present invention provides a component, dehydroeburicoic acid (TT), extracted from mycelium of *Antrodia camphorata* to treat diabetes. Accordingly, the present invention provides a new use of dehydroeburicoic acid (TT), which administrated to a subject with type 1 diabetes mellitus and hyperlipidemia has following effects.

A primary objective of the present invention is to provide a method for treating type 1 diabetes, hyperlipidemia or hepatic ballooning degeneration, comprising administering to a subject in need thereof an effective amount of the compound represented by formula (I).

Another objective of the present invention is to provide a method for decreasing mRNA levels of phosphoenol pyruvate carboxykinase (PEPCK), glucose-6-phosphatase (G6 Pase), sterol regulatory element binding protein 1c (SREBP1c), diacylglycerol acyltransferase 2 (DGAT2), and SREBP2, but increasing expression levels of peroxisome proliferator activated receptor α (PPARα) and mRNA levels of CPT1a in a cell, comprising contacting the cell with an effective amount of this compound represented by formula (I).

Formula (I)

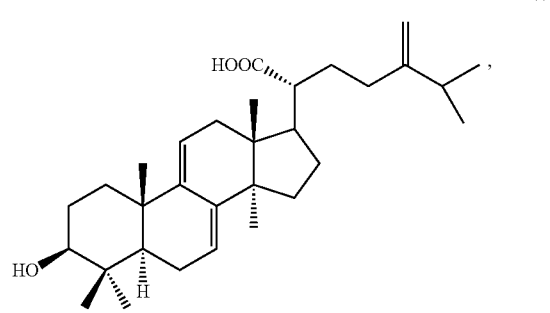

(I)

Another objective of the present invention is to provide a method for increasing expression levels of membrane glucose transporter 4 (GLUT4) in skeletal muscle and phospho-AMPK in both skeletal muscle and liver tissue, comprising contacting the tissue with an effective amount of this compound represented by formula (I).

According to an embodiment of the present invention, this compound is obtained from *Antrodia camphorata*, and this compound is dehydroeburicoic acid (TT).

According to an embodiment of the present invention, the effective amount of this compound given is from 10 mg/kg to 40 mg/kg per day.

According to an embodiment of the present invention, the cell or tissue is obtained from a subject with type 1 diabetes mellitus.

According to an embodiment of the present invention, this compound treats diabetes by decreasing blood glucose levels, and increasing insulin concentration.

According to an embodiment of the present invention, the cell or tissue is obtained from a subject with a condition of hyperlipidemia, hypertriglyceridemia, and hypercholesterolemia.

According to an embodiment of the present invention, this compound treats hepatic lipid accumulation induced by streptozotocin (STZ) to reduce hepatic ballooning degeneration.

According to an embodiment of the present invention, this compound treats hyperleptinemia induced by streptozotocin (STZ) to reduce blood leptin levels.

The present invention provides a method for treating diabetes, hyperlipidemia or hepatic total lipids by using dehydroeburicoic acid (TT), this compound can significantly lower the blood markers, such as blood glucose, total cholesterol (TC), triglyceride (TG), and leptin levels in subjects with type 1 diabetes, hyperlipidemia or hepatic ballooning degeneration. Therefore, the method of the present invention provides a new strategy to prevent and treat type 1 diabetes mellitus, hypertriglyceridemia, or hypercholesterolemia.

According to an embodiment of the present invention, this compound treats hyperglycemia by increasing expression levels of GLUT4 and phospho-Akt in vitro and enhancing membrane GLUT4 in skeletal muscle, and increasing phospho-AMPK protein expression in skeletal muscle and liver, but decreasing mRNA levels of PEPCK and G6 Pase, thus lowering blood glucose levels.

According to an embodiment of the present invention, this compound treats hypertriglyceridemia, and hepatic steatosis through inhibition of hepatic fatty acid synthase (FAS) and peroxisome proliferator activated receptor γ (PPARγ) accompanied by reduced sterol response element binding protein-1c (SREBP1c) and diacyl glycerol acyltransferase 2 (DGAT2) mRNA levels, but increases expression levels of peroxisome proliferator activated receptor α (PPARα) accompanied by enhanced carnitine palmitoyltransferase-1a (CPT1a) mRNA levels increase fatty acids oxidation in the liver.

According to an embodiment of the present invention, this compound treats hypercholesterolemia by decreasing SREBP2 mRNA levels, thus leading to a decrease in blood total cholesterol (TC) levels.

According to an embodiment of the present invention, this compound treats hyperglycemia partly by insulin-dependent pathway and partly dependently be insulin-independent pathway, thus leading to a decrease in blood glucose levels.

According to an embodiment of the present invention, this compound treats hepatic steatosis and reduce ballooning of hepatocyte, by decreasing adipose and hepatic lipogenic genes expression of PPARγ and FAS, but increasing PPARα, which may contribute to decreasing lipid accumulation both in adipose and liver tissue.

The effects of dehydroeburicoic acid on STZ-induced diabetes and other related deceases are as follows:

1) TT-treated mice (at doses of 10, 20, 40 mg/kg/day) markedly decreased blood glucose levels.

2) STZ-induced diabetic mice treated with TT displayed a decrease in circulating triglyceride (TG) and total cholesterol (TC) levels, indicating TT ameliorated diabetes and dyslipidemia.

3) Membrane skeletal muscular expression levels of glucose transporter 4 (GLUT4) and expression levels of AMPK phosphorylation (phospho-AMPK) in both liver and skeletal muscle were increased in STZ-induced diabetic mice through TT treatment, indicating TT is effective in ameliorating hyperglycemia.

4) The process of treating and ameliorating the hyperglycemia with TT is accompanied with a decrease in mRNA levels of phosphoenolpyruvate carboxykinase (PEPCK) and glucose-6-phosphatase (G6 Pase), which was related to the inhibition of hepatic glucose production and attenuating diabetic state.

5) TT also showed anti-hyperlipidemic effect by increasing hepatic expression levels of peroxisome proliferator-activated receptor α (PPARα) and mRNA levels of CPT-1a.

6) TT decreased expression levels of fatty acid synthase (FAS), which further contributed to a decrease in circulating TG levels.

7) TT-treated mice displayed decreased SREBP2 mRNA levels and reduced blood TC levels. These findings strongly support that TT prevents diabetic and dyslipidemic states in STZ-induced diabetic mice evidenced by regulation of GLUT4, PPARα, FAS, and phosphorylation of AMPK.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there are illustrated preferred embodiments of the invention.

DETAILED DESCRIPTION

Figure 1:
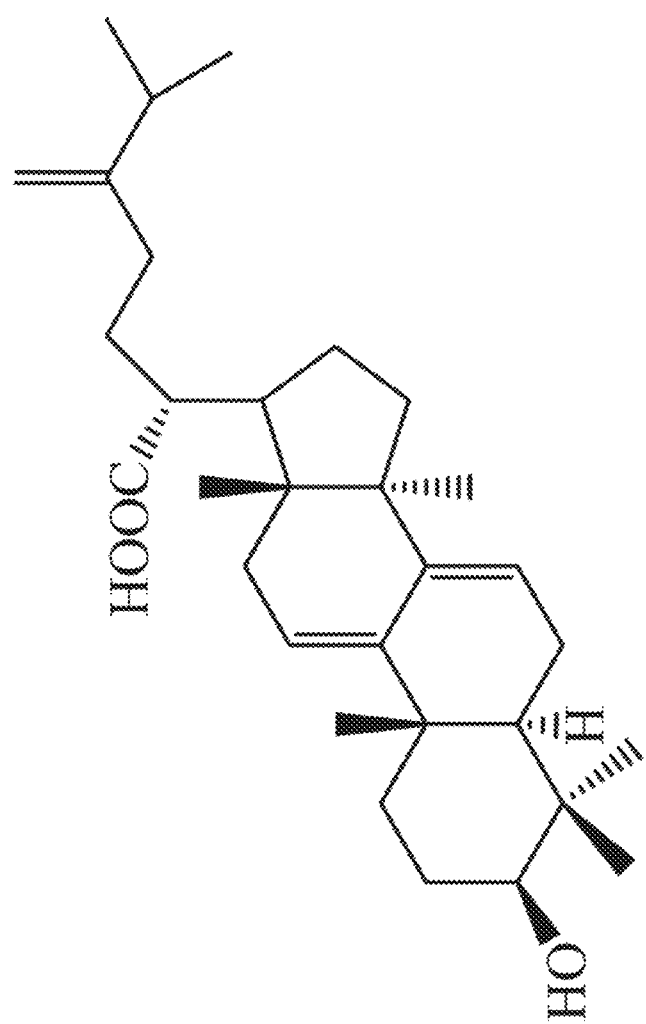
FIG. 1 shows a chemical structure of dehydroeburicoic acid (TT)

The present invention will be clearer from the following description when viewed together with the accompanying drawings, which show, for purpose of illustrations only, the preferred embodiment in accordance with the present invention.

The present invention relates to the new use of active ingredient-dehydroeburicoic acid (TT) extracted from *A. camphorata*, and its derivatives used for production of pharmaceutical compounds which are used to decrease plasma TG (triglycerides), hepatic steatosis, and total cholesterol levels, and treat diabetes.

*Antrodia camphorata* extract refers to freeze-dried powders of the mycelia of AC: TT. Freeze-dried powders of the mycelia of AC (3.0 kg) were extracted three times with methanol (12 L) at room temperature (4 days×3). The methanol extract was evaporated in vacuo to give a brown residue, which was suspended in $H_2O$ (1 L) and then partitioned with ethyl acetate (1 L×3). The EtOAc fraction (200 g) was chromatographed on silica gel using mixtures of hexane and EtOAc of increasing polarity as eluents and further purified with HPLC. TT was isolated by HPLC on a Hibar prepacked column RT 250-10 with chloroform/ethyl acetate (7:1) and a refractive index (RI) (Knauer RI detector 2400). The flow rate was 3 mL/min, and the injection volumes of samples were 100 µL. The yields of TT obtained were about 0.2% (w/w). The purity of TT was >99%.

FIG. 1 shows the chemical structure of TT, and the determination of spectral data of TT is as follows: $^1$H NMR (300 MHz, pyridine-$d_5$) δ 1.90 (2H, m, H-2), 3.43 (1H, t, J=7.5 Hz, H-3), 1.26 (1H, m, H-5), 2.16 (2H, m, H-6), 5.61 (1H, d, J=5.2 Hz H-7), 5.36 (1H, d, J=5.1 Hz, H-11), 2.50 (1H, H-12a), 2.33 (1H, br s, H-12(3), 1.02 (3H, s, H-18), 1.08 (3H, s, H-19), 2.64 (1H, td, J=11.0, 3.0 Hz, H-20), 2.29 (1H, m, H-25), 1.03, 1.04 (3H each, d, J=7.5 Hz, H-26 and H-27), 4.88 (1H, br s, H-28a), 4.92 (1H, br s, H-28(3), 1.09 (3H, s, H-29), 1.22 (3H, s, H-30), and 1.14 (3H, s, H-31).

First Part: Cell Culture.

The next paragraph describe how to determine whether TT directly regulated GLUT4 protein expression in cultured C2C12 myotube cells incubated with either insulin or TT.

C2C12 skeletal myoblasts (ATCC, CRL-1772) were maintained in growth media consisting of Dulbecco's modified Eagle's medium (DMEM) (Gibco BRL) supplemented with 10% fetal bovine serum (FBS) (Hyclone) and 100 U/mL penicillin/100 µg/mL streptomycin (Gibco BRL) and split 1:4 using 0.05% trypsin when 80% confluent. Myoblasts were diluted and placed in a 9 cm dish. Cells were cultured to achieve 80-90% confluency, and growth medium was changed as 2% FBS/DMEM every 24 h for 5-7 days.

Determination of GLUT4 and phospho-Akt (Ser$^{473}$)/Total Akt Proteins in Vitro: Differentiated C2C12 cells were serum starved in DMEM/BSA (2 h at 37° C.) prior to incubation either with test compounds (TT at 1, 5, 10, and 25 µg/mL) or with vehicle (DMSO containing saline, final concentration of DMSO=0.2%) for 30 min or with 100 nM insulin for 25 min.

Following treatment, cells were washed three times with ice-cold PBS and separated into two portions. A portion of the cells was subsequently lysed in RIPA buffer (50 mM Tris-HCl, pH 8, 150 mM NaCl, 1% NP-40, 0.5% sodium deoxycholate, 0.1% SDS) supplemented with complete protease inhibitor cocktail (Roche) and phosphatase inhibitors and then centrifuged at 20000 g for 200 min.

Supernatant protein was collected and stored at −20° C. Another portion of cells was homogenized with buffer (250 mmol/L sucrose, 50 mmol/L Tris, and 0.2 mmol/L edetic acid, pH 7.4) at 4° C., as previously described. The homogenates were centrifuged at 9000 g for 10 min (4° C.). The pellet was suspended with 0.5 mL of homogenization buffer and then centrifuged, repeated three times. The three supernatants were collected, mixed, and centrifuged at 190000 g for 60 min (4° C.). The pellet was resuspended with 0.2 mL of homogenization buffer, stored at −20° C., and performed within membrane.

Protein concentration was determined via BCA assay (Pierce). Equal amounts of protein were then diluted four times in SDS sample buffer and subjected to SDS-PAGE and were detected by Western blotting with antibodies specific for Akt, phosph-Akt $Ser^{473}$, and GLUT4. The density blotting was analyzed using Alpha Easy FCsoftware (Alpha Innotech Corp., Randburg, South Africa).

Second Part: Experimental Animal Model

Fenofibrate is a PPARα agonist which has been used in the treatment of hypertriglyceridemia for many years. PPARα is a key lip metabolism related regulator for reducing TG and fatty acid through regulation of lipogenesis, fatty acid oxidation, and energy metabolism.

Metformin is an anti-diabetes drug widely used in the treatment of the type 2 diabetes, and capable of activating AMPK in the liver and skeletal muscles. Although Metformin may lead to side effects, including lactic acidosis, it is thought to have a potential role in the treatment of type 1 diabetes.

Therefore, fenofibrate and metformin are selected as comparative drugs. To assess whether changes in glycemia regulated GLUT4, and phospho-AMPK expression in vivo, Phosphorylation of $Thr^{172}$ of α subunits is essential for AMPK activity, we studied skeletal muscle and liver tissue from STZ-induced diabetic mice, an animal model of type 1 diabetes, we also investigated whether TT regulated expression of genes involved in antidiabetes, lipogenesis, and triglyceride lipase in the liver tissue, including phosphoenolpyruvate caboxykinase (PEPCK), glucose 6-phosphoatase (G6 Pase), peroxisome proliferator-activated receptor (PPAR) a, fatty acid synthase (FAS), and diacyl glycerol acyltransferase 2 (DGAT2).

What follows is the description of the effect of the active ingredient-TT extracted from AC on the prevention or treatment of diabetes, a experimental animal model, and the mice blood data, serum biochemical analysis, histopathological analysis, hepatic lipid analysis, RNA extraction, and relative quantitation of mRNA indicating Gene expression.

2-1 Animal Model and Experimental Design

Male C57BL/6J mice, at the age of 4 weeks, were obtained from the National Laboratory Animal Breeding and Research Center, Ministry of Science and Technology. The study protocol was approved by the guidelines of the Institutional Animal Care and Use Committee of Central Taiwan University of Science and Technology. The study protocol was performed as previously described.[28] Diabetes was induced by intraperitoneal injection of streptozotocin (Sigma Chemical, St. Louis, Mo., USA) for 5 consecutive days. The dosage of STZ was 55 mg/kg (dissolved in 0.05 M cold sodium citrate buffer, pH 4.5). The normal control mice received only citrate buffer of the same volume. After 2 weeks, the mice with severe diabetes exhibiting hyperglycemia (fasting blood glucose range of >250 mg/dL) were considered as diabetic and selected for the experiment.

Diabetic mice were randomly divided into five groups and were treated with either vehicle (distilled water), TT (TT1: 10, TT2:20, or TT3:40 mg/kg), metformin (300 mg/kg), or fenofibrate (Feno) (250 mg/kg) in a similar volume. The vehicle, TT, Metf, or Feno was administered by oral gavage one time per day for another 28 days. During the experiment, all mice were fasted overnight, and blood was collected from the retro-orbital sinus. After dosing for 4 weeks, food was removed from the mice at night, and on the next day, the mice after 12 h of fasting were sacrificed. All of the individual tissues were collected and weighed, and parts of tissues were instantly frozen at −80° C. for later target gene analysis.

2-2 Fasting Blood Glucose and Biochemical Parameters Assay:

A portion of the acquired blood samples (0.8 mL) was immediately taken for analysis of blood glucose level and a portion for analysis of TG, total cholesterol (TC), and free fatty acids.

2-3 Adipocytokine Levels Assay:

The levels of blood insulin, leptin, and adiponectin were analyzed using a commercial assay kit (mouse insulin ELISA kit, Mercodia, Uppsala, Sweden; mouse leptin ELISA kit, Morinaga, Yokohama, Japan; Mouse Adiponectin ELISA kit, Crystal Chem International, Downers Grove, Ill., USA) as previously described.

2-4 Histology:

Parts of EWAT and liver tissue specimens were investigated as previously described.[31,32] Microscopic images were taken using a microscope (Olympus BX51, BX51, Olympus, Tokyo, Japan).

2-5 Relative Quantization of mRNA Indicating Gene Expression Assay:

Total RNA from liver tissue was isolated with a Trizol Reagent (Molecular Research Center, Inc., Cincinnati, Ohio) according to the manufacturer's directions. The integrity of the extracted total RNA was examined by 2% agarose gel electrophoresis, and the RNA concentration was determined by the ultraviolet (UV) light absorbency at 260 nm and 280 nm (Spectrophotometer U-2800A, Hitachi). Total RNA (1 μg) was reverse transcribed to cDNA in a reaction mixture containing buffer, and 5 μL Moloney murine leukemia virus reverse transcriptase (Epicentre, Madison, Wis., USA). The polymerase chain reaction (PCR) was performed in a final 25 μL containing 1 U Blend Taq-Plus (TOYOBO, Japan), 1 μL of the RT first-strand cDNA product, 10 μM of each forward (F) and reverse (R) primer, 75 mM Tris-HCl (pH 8.3) containing 1 mg/L Tween 20, 2.5 mM dNTP, and 2 mM $MgCl_2$. The primers are shown in Table 1. The products were run on 2% agarose gels and stained with ethidium bromide.

TABLE 1

| gene | Forward primer and reverse primer | PCR product (bp) | Annealing temperature (° C.) (annealing temp) |
|---|---|---|---|
| PEPCK | F: CTACAACTTCGGCAAATACC<br>R: TCCAGATACCTGTCGATCTC<br>(Seq No. NM_011044.2) | 330 | 51 |
| G6-Pase | F: GAACAACTAAAGCCTCTGAAAC<br>R: TTGCTCGATACATAAAACACTC<br>(Seq No. NM_008061.3) | 350 | 50 |
| PPARα | F: ACCTCTGTTCATGTCAGACC<br>R: ATAACCACAGACCAACCAAG<br>(Seq No. NM_011144) | 352 | 49 |
| SREBP-1c | F: GGCTGTTGTCTACCATAAGC<br>R: AGGAAGAAACGTGTCAAGAA<br>(Seq No. NM_011480) | 219 | 48 |
| DGAT2 | F: AGTGGCAATGCTATCATCATCGT<br>R: AAGGAATAAGTGGGAACCAGATCA<br>(Seq No. NM_026384.3) | 149 | 50 |

TABLE 1-continued

| gene | Forward primer and reverse primer | PCR product (bp) | Annealing temperature (° C.) (annealing temp) |
|---|---|---|---|
| CPT1a | F: GCAGGAAATTTACCTCTGTG<br>R: ACATGAAGGGTGAAGATGAG<br>(Seq No. NM_153679) | 288 | 51 |
| SREBP-2 | F: ATATCATTGAAAAGCGCTAC<br>R: ATTTTCAAGTCCACATCACT<br>(Seq No. AF289715.2) | 256 | 48 |
| GAPDH | F: TGTGTCCGTCGTGGATCTGA<br>R: CCTGCTTCACCACCTTCTTGA<br>(Seq No. NM_008084.3) | 99 | 55 |

2-6 Western Blotting Assay.

Protein extractions and immunoblots for the determination of GLUT4 and phospho-AMPK (Thr$^{172}$) proteins were performed by skeletal muscle and liver tissue of mice and have been described in detail elsewhere. PPARα, PPARγ, and FAS proteins were performed by the liver and white adipose tissue of mice. Skeletal muscle from mice was subjected to GLUT4 expression level analysis, and the total membrane fractions were collected with buffer and determined using a described procedure. The protein contents of GLUT4, phospho-AMPK, and total AMPK were detected by Western blotting and determined as described.

3. Results

Figure 2A:
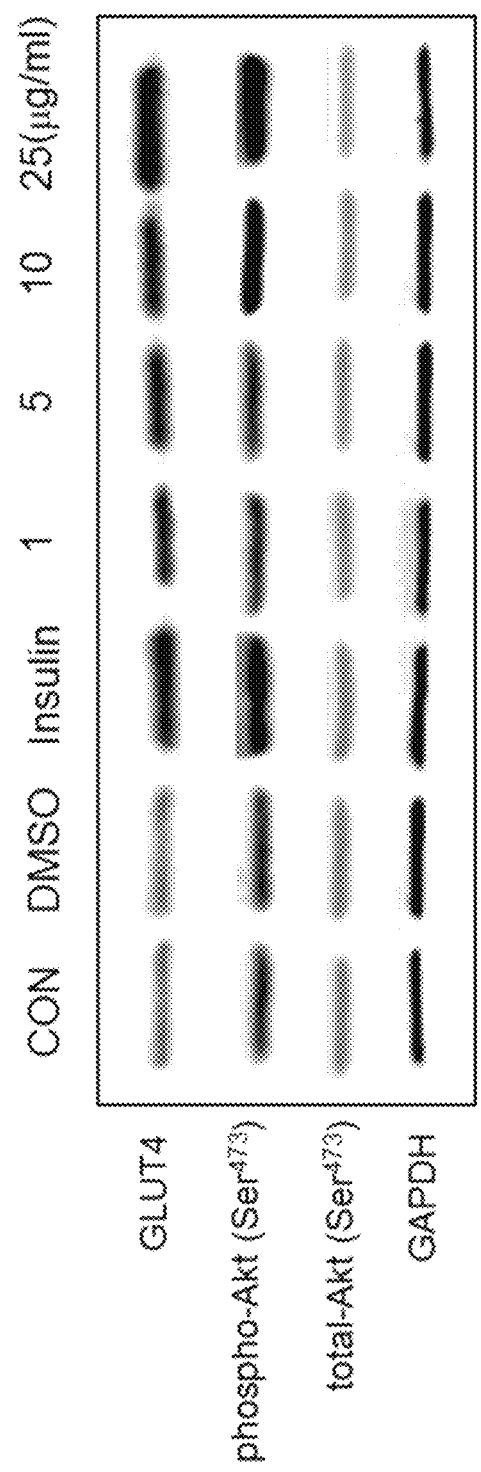
FIG. 2A effect of dehydroeburicoic acid (TT) on GLUT4 and phospho-Akt/total-Akt in vitro: (A) representative blots for TT in C2C12 myoblastscells.
Figure 2B:
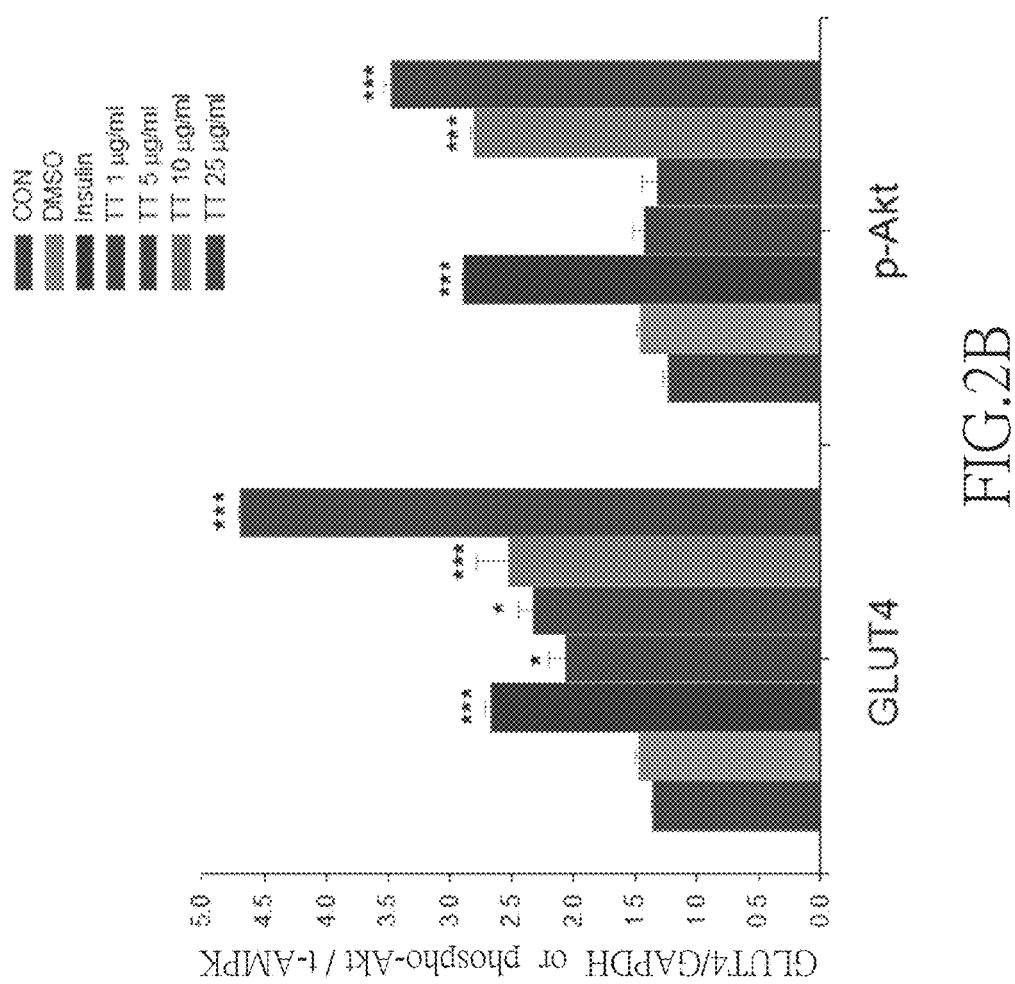
FIG. 2B quantification of the GLUT4 protein contents and the ratio of phospho-Akt to total Akt, C2C12 skeletal myoblasts cells were treated with TT compounds as described under Materials and Methods, and equal amounts of lysates were resolved by SDS-PAGE and blotted for GLUT4, Akt, and phospho-Akt (Ser$^{473}$)

The experimental results of the STZ-induced mice in the cell culture-shown in the FIGS. 2A and 2B. The cell culture include the GLT4, phospho-Akt (Ser$^{473}$) total-Akt (Ser$^{473}$) and GAPDH protein contents of the C2C12 cells in the CON, DMSO, Insulin, TT (1 µg/mL), TT (5 µg/mL) and TT groups (10 µg/mL). The animal model includes: the STZ-induced diabetic mice's body weight (Table 2), the pathological section of the epididymal white adipose tissue or liver tissue (FIGS. 3A, 3B), the semiquantative RT-PCR analysis on PEPCK, G6 Pase, PPARα, SREBP1c, DGAT2, CPT1a, and SREBP2 mRNA levels in liver tissue of the mice (FIGS. 4A, 4B, 4C), the determination of GLUT4 and phospho-AMPK (Thr$^{172}$), the total-AMPK (Thr$^{172}$), GAPDH protein contents in the skeletal muscles of the mice (FIGS. 5A and 5B), the determination of the phospho-AMPK (Thr$^{172}$), the total-AMPK (Thr$^{172}$), and the β-actin protein contents in the liver of the mice (FIGS. 5A and 5B), the determination of the GAPDH, FAS, PPAR γ, and β-actin protein contents in the liver of the mice (FIGS. 6A, 6B and 6C), and the determination of the GAPDH, FAS, PPARγ, and β-actin protein contents in the adipose tissue of the mice (FIGS. 6A, 6B and 6C).

FIGS. 2A, 2B and table 2 show the protein analysis on the C2C12 skeletal cells after the cell culture. The CON (control group) refers to the blank control group cultured in the DMEM, the DMSO (DMSO group) refers to the control group cultured in the DMSO, and the insulin (insulin group) refers to an experimental group cultured with insulin. 1, 5, 10, and 25 µg/mL refer to different TT treated experimental groups (which are hereinafter referred to as TT groups 1, 5 and 10) treated with different concentrations of active ingredients. (*) P<0.05, (* *) P<0.01, and (* * *) P<0.001 compared with the control group.

FIGS. 2A and 2B show the Akt (Ser$^{473}$)/Total Akt in vitro. At the end of the cell culture, the protein expressions of GLUT4 were higher in the insulin- and TT-treated groups 1, 5, 10 and 25 than in the CON group in C2C12 myotube cells (Insulin group: P<0.001, TT group 1: P<0.05, TT group 5: P<0.05, TT group 10: P<0.001, and TT group 25: P<0.001, respectively). The levels of phospho-Akt (Ser$^{473}$)/total Akt proteins were higher in the insulin- and TT-treated groups 10, 25 than in the CON group (insulin group: P<0.001, TT group 10: P<0.001, and TT group 25: P<0.001, respectively).

TABLE 2

| parameters | CON | STZ | STZ + TT1 10$^a$ | STZ + TT2 20$^a$ |
|---|---|---|---|---|
| Tissue weight (wt %) | | | | |
| EWAT (wt %) | 1.140 ± 0.058 | 0.947 ± 0.104 | 0.778 ± 0.063 ## | 0.783 ± 0.087 ## |
| MWAT (wt %) | 0.784 ± 0.100 | 0.692 ± 0.080 | 0.562 ± 0.114 | 0.709 ± 0.111 |
| RWAT (wt %) | 0.152 ± 0.028 | 0.099 ± 0.012 | 0.122 ± 0.029 | 0.161 ± 0.031 |
| Visceral fat (wt %) | 1.292 ± 0.078 | 1.046 ± 0.102 | 0.900 ± 0.082 # | 0.944 ± 0.115 # |
| Skeletal muscle (wt %) | 0.934 ± 0.066 | 1.235 ± 0.095 # | 1.162 ± 0.097 | 1.112 ± 0.096 |
| liver (wt %) | 3.505 ± 0.140 | 3.678 ± 0.107 | 3.952 ± 0.138 | 3.966 ± 0.171 |
| spleen (wt %) | 0.222 ± 0.017 | 0.207 ± 0.007 | 0.213 ± 0.019 | 0.193 ± 0.021 |
| BAT (wt %) | 0.162 ± 0.022 | 0.252 ± 0.037 | 0.296 ± 0.012 ### | 0.323 ± 0.026 ### |
| Weight gain (g) | 2.69 ± 0.32 | 2.99 ± 0.21 | 2.73 ± 0.38 | 2.36 ± 0.27 |
| Final weight (g) | 23.05 ± 0.91 | 22.11 ± 0.47 | 22.99 ± 0.43 | 20.91 ± 0.59 |
| Food intake (g/day/mouse) | 3.08 ± 0.06 | 3.15 ± 0.04 | 3.06 ± 0.04 | 3.12 ± 0.05 |
| Blood profiles | | | | |
| Plasma free fatty acid | 1.18 ± 0.12 | 1.09 ± 0.21 | 0.76 ± 0.07 *## | 0.74 ± 0.12 **## |
| Blood glucose (mg/dL) | 85.1 ± 3.3 | 180.1 ± 5.3 ### | 103.3 ± 3.2 ***# | 97.3 ± 2.7 *** |
| TG (mg/dL) | 85.05 ± 2.83 | 97.94 ± 2.47 ### | 88.71 ± 1.40 * | 86.65 ± 1.53 ** |
| Total cholesterol (mg/dL) | 95.96 ± 2.05 | 134.13 ± 5.40 ### | 94.42 ± 2.49 *** | 92.87 ± 1.72 *** |
| insulin (µg/L) | 2.373 ± 0.023 | 1.935 ± 0.041 ## | 2.222 ± 0.060 * | 2.426 ± 0.078 *** |
| Adiponectin (µ/mL) | 3.073 ± 0.017 | 2.538 ± 0.014 ## | 2.982 ± 0.019 * | 3.020 ± 0.026 ** |
| Leptin (ng/mL) | 27.635 ± 6.169 | 292.534 ± 10.572 | 192.275 ± 17.341 | 122.114 ± 24.854 |

| parameters | STZ + TT3 40$^a$ | STZ + Metf 300$^a$ | STZ + Feno 250$^a$ |
|---|---|---|---|
| Tissue weight (wt %) | | | |
| EWAT (wt %) | 0.715 ± 0.068 ###* | 0.956 ± 0.047 | 0.743 ± 0.059 ## |
| MWAT (wt %) | 0.720 ± 0.114 | 0.758 ± 0.064 | 0.795 ± 0.070 |
| RWAT (wt %) | 0.119 ± 0.014 | 0.176 ± 0.023 | 0.154 ± 0.016 |

TABLE 2-continued

| | | | |
|---|---|---|---|
| Visceral fat (wt %) | 0.834 ± 0.082 ## | 1.132 ± 0.054 | 0.889 ± 0.075 # |
| Skeletal muscle (wt %) | 1.128 ± 0.110 | 1.208 ± 0.149 | 1.292 ± 0.076 # |
| liver (wt %) | 4.366 ± 0.153 **### | 4.168 ± 0.100 ## | 4.016 ± 0.127 *# |
| spleen (wt %) | 0.215 ± 0.017 | 0.230 ± 0.007 | 0.202 ± 0.017 |
| BAT (wt %) | 0.378 ± 0.020 **### | 0.369 ± 0.018 *### | 0.319 ± 0.030 ### |
| Weight gain (g) | 1.66 ± 0.44 | 2.32 ± 0.25 | 1.94 ± 0.08 |
| Final weight (g) | 21.00 ± 0.56 | 22.02 ± 0.62 | 22.39 ± 0.78 |
| Food intake (g/day/mouse) | 3.09 ± 0.07 | 3.14 ± 0.04 | 3.07 ± 0.09 |
| Blood profiles | | | |
| Plasma free fatty acid | 0.69 ± 0.05 ***### | 0.74 ± 0.09 **## | 0.71 ± 0.10 ***### |
| Blood glucose (mg/dL) | 96.4 ± 3.0 *** | 104.1 ± 4.3 ***## | 102.1 ± 4.2 ***# |
| TG (mg/dL) | 78.55 ± 2.80 *** | 86.34 ± 2.39 ** | 85.37 ± 1.19 ** |
| Total cholesterol (mg/dL) | 89.74 ± 2.82 *** | 100.39 ± 8.12 *** | 104.40 ± 3.00 *** |
| insulin (μg/L) | 2.642 ± 0.066 ***# | 2.490 ± 0.054 *** | 2.551 ± 0.097 *** |
| Adiponectin (μ/mL) | 3.215 ± 0.032 **## | 3.015 ± 0.031 ** | 3.007 ± 0.038 ** |
| Leptin (ng/mL) | 121.787 ± 22.136 | 185.985 ± 30.697 | 139.700 ± 32.596 | note:
$^a$dose (mg/kg/day) ° STZ + TT1: TT, 10 mg/kg/day; STZ + TT2: TT, 20 mg/kg/day; STZ + TT3: TT, 40 mg/kg/day; STZ + Metf: Metf, 300 mg/kg/day; STZ + Feno: Feno, 250 mg/kg/day °

FIGS. 3A-6C and table 2 show the tissue and blood data analysis results of the STZ-induced type 1 diabetic mice which are fed with different doses of TT, Metf or Feno, wherein the CON (control group) refers to the blank control group, the STZ (STZ group) refers to the STZ-induced control group, the STZ+TT1, STZ+TT2, STZ+TT3 refer to different experimental groups (which are hereinafter referred to as TT groups STZ+TT1, STZ+TT2, and STZ+TT3) treated with different doses of dehyroeburicoic acid, STZ+Metf refers to an experimental STZ-induced group (which is hereinafter referred to as STZ+Metf group) treated with Metf, and STZ+Feno refers to an experimental STZ-induced group (which is hereinafter referred to as STZ+Feno group) treated with Feno. (#) P<0.05, (##) P<0.01, and (###) P<0.001 compared with the control group CON, and (*) P<0.05, () P<0.01, and (*) P<0.001 compared with the control group STZ+water (vehicle).

Body Weight, Body Weight Gain, Food Intake, and Tissue Weight:

The body weight of all mice when they entered the animal room was 15.03±0.17 g. The mice were induced by STZ at constant temperature, humidity and light for seven days, and then treated with TT for 4 weeks. After acclimatization, and at the beginning of STZ induction, body weights were 18.55±0.19 g. At the beginning of dosing, the body weight of the CON group was 20.36±0.76 g and that of the STZ mice was 19.59±0.22 g. At the end of the experiment, there was no significant difference in body weight and food intake between the STZ-induced mice and the CON group (Table 2).

There are mice of different TT groups fed with different doses (which are all referred to as STZ+TT, including groups of TT1 treated with a dose of 10 mg/kg/day, TT2 with dose of 20 mg/kg/day, TT3 treated with a dose of 40 mg/kg/day), Metformin group (Metf group treated with a dose of 300 mg/kg/day) and Fenofibrate group (Feno group treated with a dose of 250 mg/kg/day). Following the treatment, the body weight and food intake of TT-, Metf-, and Feno-treated groups did not differ from the STZ group. Treatment with TT3 and Feno decreased body weight gain (P<0.01 and P<0.05, respectively). TT3 and Feno treatment increased the liver weights compared with the STZ group (P<0.01 and P<0.05, respectively). TT3, Metf, and Feno treatment showed an increase in the weights of the liver compared with the CON group (P<0.001, P<0.01, and P<0.05, respectively). TT3 and Metf treatment showed an increase in the weights of brown adipose tissue (BAT) compared with the STZ group (P<0.05 and P<0.05, respectively).

Plasma Glucose Levels:

At the beginning of the study, all of the mice started with similar blood glucose levels (85.7±3.7 mg/dL). After STZ induction, blood glucose levels of the CON group were 87.1±4.9. STZ-induced diabetic mice with blood glucose levels >240 mg/dL were selected for the experiment, and the glucose levels of the STZ diabetic mice were 259.8±3.8 mg/dL. At the end of the experiment, the glucose levels of the STZ group were significantly greater than those of the CON group (P<0.001). Treatment with TT1, TT2, TT3, Metf, or Feno showed a significant reduction in plasma glucose as compared with the STZ group (P<0.001, P<0.001, P<0.001, P<0.001, and P<0.001, respectively). Treatment with TT2 or TT3 did not differentiate the CON group in blood glucose levels (Table 2).

Plasma Lipid:

At the end of the experiment, the levels of TG and TC were greater in the STZ group than those in the CON group (P<0.001 and P<0.001, respectively) (Table 2). TT1, TT2, TT3, Metf, or Feno treatment reduced free fatty acid levels compared with the STZ group (Table 2). Treatment with TT1, TT2, TT3, Metf, or Feno decreased the concentrations of TG as compared with the STZ group (P<0.05, P<0.01, P<0.001, P<0.01, and P<0.01, respectively). TT1, TT2, TT3, Metf, or Feno treatment reduced TC levels compared with the STZ group (P<0.001, P<0.001, P<0.001, P<0.001, and P<0.001, respectively). Treatment with TT1, TT2, TT3, Metf, or Feno did not differ from the CON group in both blood TG and TC levels (Table 2).

Insulin, Leptin, and Adiponectin Levels:

The concentrations of insulin were lower in the STZ group than in the CON group (P<0.01). TT1-, TT2-, TT3-, Metf-, or Feno-treated groups significantly increased insulin levels as compared with the STZ group (P<0.05, P<0.001, P<0.001, P<0.001, and P<0.001, respectively) (Table 2). Treatment with TT3 increased blood insulin levels as compared with the CON group (P<0.05). The concentrations of leptin were higher in the STZ group than in the CON group (P<0.001). TT1-, TT2-, TT3-, Metf-, or Feno-treated groups significantly decreased leptin levels as compared with the STZ group (P<0.05, P<0.001, P<0.001, P<0.05, and P<0.001, respectively) (Table 2). The concentrations of adiponectin were lower in the STZ group than in the CON group (P<0.05). TT1-, TT2-, TT3-, Metf-, and Feno-treated groups significantly increased the levels of adiponectin as compared with the STZ group (P<0.05, P<0.01, P<0.01, P<0.01, and P<0.01, respectively) (Table 2).

Figures 3A, 3B:
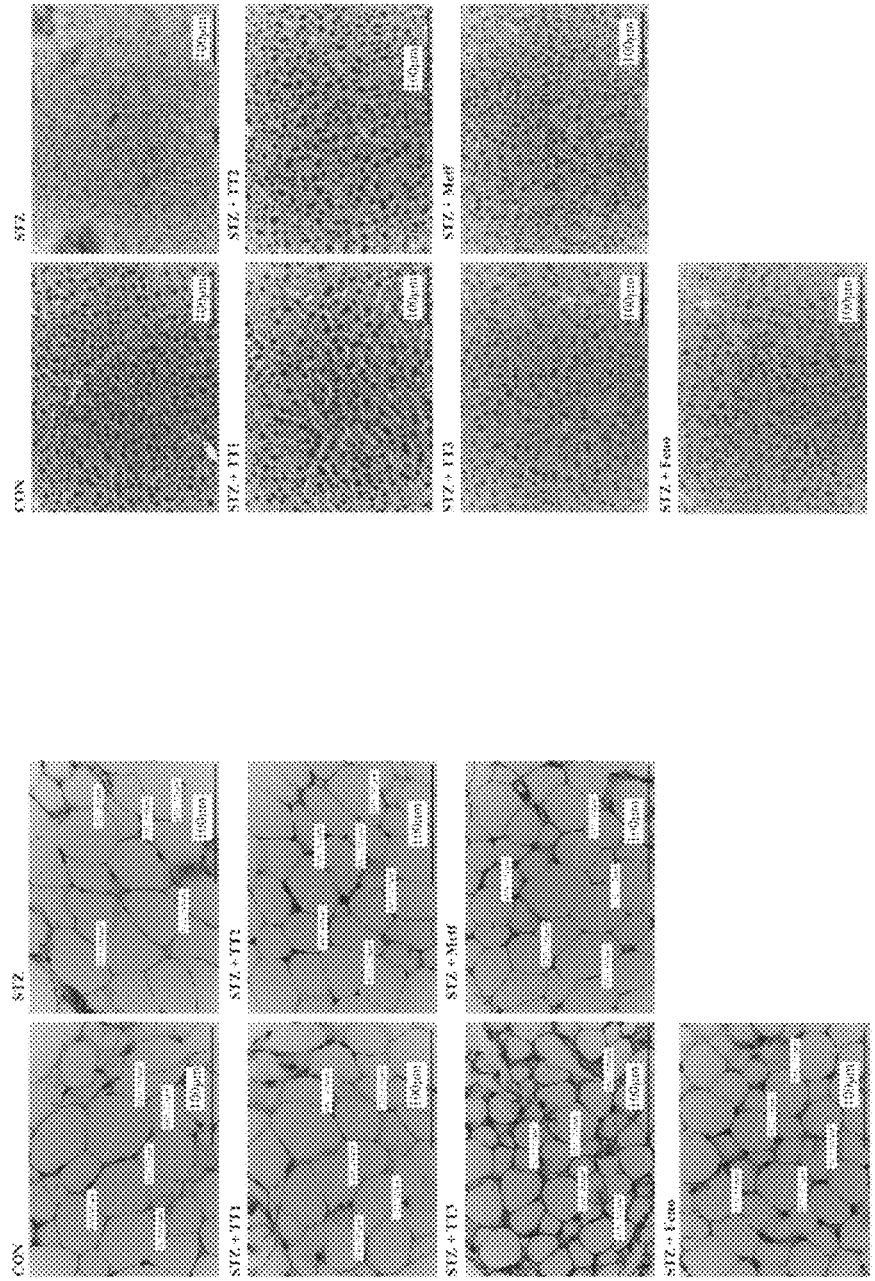
FIG. 3A Histology of epididymal white adipose tissue (WAT) of mice in the control (CON), streptozotocin plus vehicle (distilled water) (STZ), STZ+TT1, STZ+TT2, STZ+TT3, STZ+metformin (Metf), or STZ+fenofibrate (Feno) groups by hematoxylin and eosin staining. Magnification: 10 (ocular)×20 (object lens)
FIG. 3B Histology of liver tissue of mice in the control (CON), streptozotocin plus vehicle (distilled water) (STZ), STZ+TT1, STZ+TT2, STZ+TT3, STZ+metformin (Metf), or STZ+fenofibrate (Feno) groups by hematoxylin and eosin staining.

Histology:

STZ-induced adipocytes did not differ from the CON group in epididymal WAT (the average areas of adipocytes in the STZ group and CON group were 6274.8±188.4 and 7150.1±221.1 μm², respectively). Treatment with TT3 (4910.5±104.9 μm²) caused atrophy compared with the STZ group (FIGS. 3A and 3B). The average areas of the TT2-, Metf-, or Feno-treated mice were 5379.9±187.2, 5308.9±204.7, and 5373.8±194.6 μm², respectively. The STZ-induced group showed slight ballooning of hepatocyte compared with the CON group. Afterward, treatment with TT1, TT2, TT3, Metf, or Feno exerted no ballooning phenomenon. These morphological results strongly suggest TT did not cause hepatic TG accumulation.

Figure 4A:
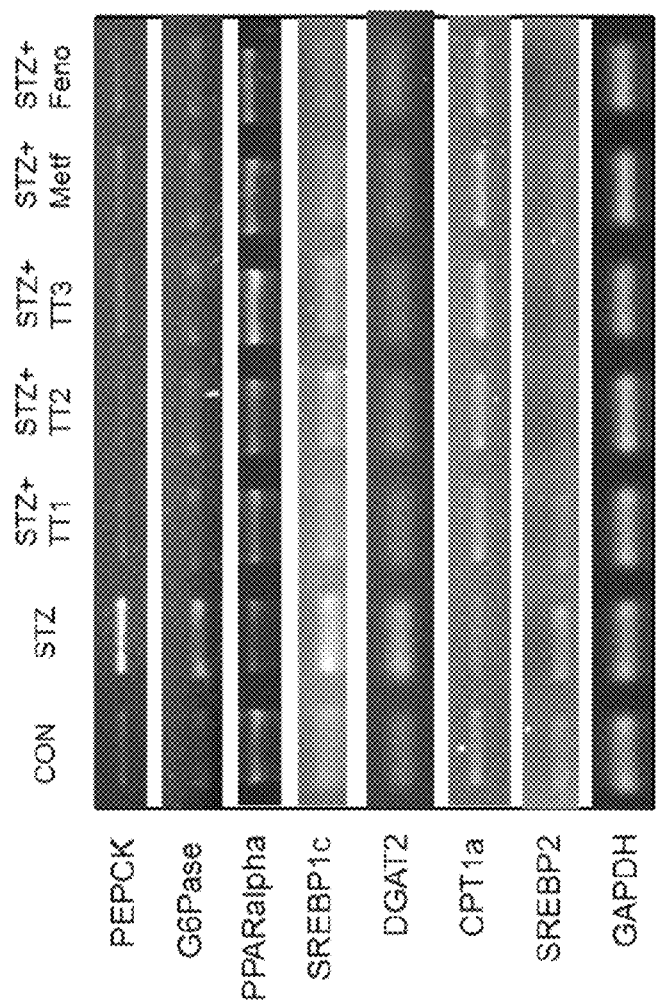
FIG. 4A is a representative image illustrating the semi-quantative RT-PCR analysis on PEPCK, G6 Pase, PPARα, SREBP1c, DGAT2, CPT1a, and SREBP2 mRNA levels in liver tissue of the mice by oral gavage dehydroeburicoic acid (TT1, TT2, TT3, 10, 20 and 40 mg/kg body weight, respectively), metformin (Metf; 300 mg/kg body weight), or fenofibrate (Feno; 250 mg/kg body weight)
Figure 4C:
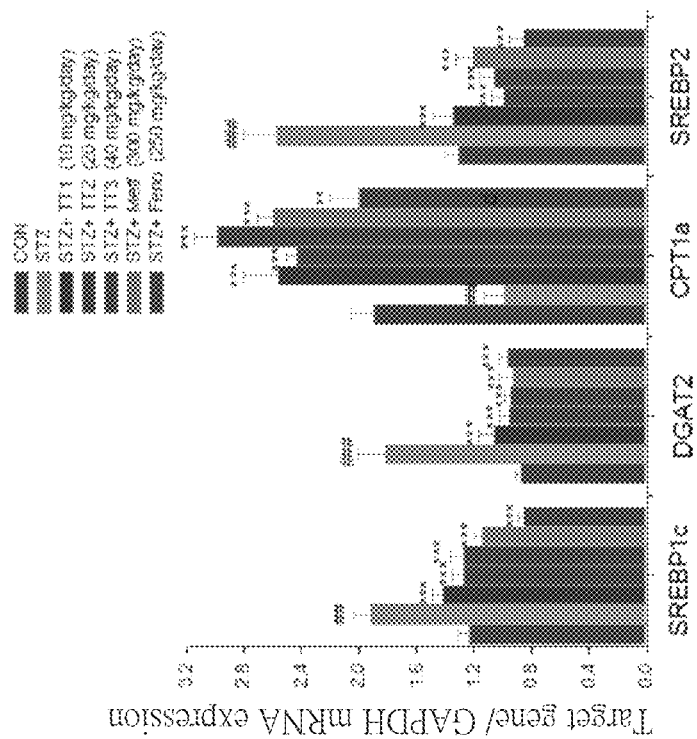
FIG. 4C shows the quantification of the ratio of target gene to GAPDH mRNA expression, total RNA (1 µg) isolated from tissue was reverse transcripted by MMLV-RT; 10 µL of RT products were used as templates for PCR. The expression levels of SREBP1c, DGAT2, CPT1a, and SREBP2 mRNA were measured and quantified by image analysis, and values were normalized to GAPDH mRNA expression.
Figure 4B:
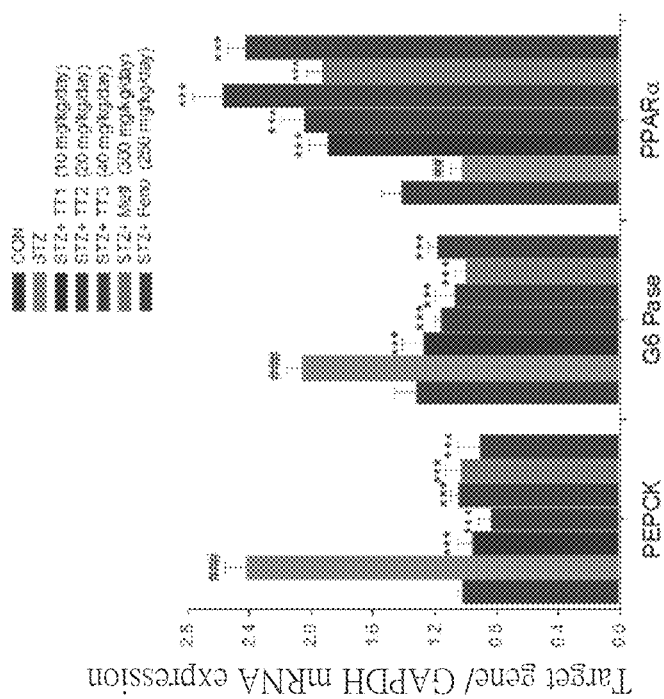
FIG. 4B shows the quantification of the ratio of target gene to GAPDH mRNA expression, total RNA (1 µg) isolated from tissue was reverse transcripted by MMLV-RT; 10 µL of RT products were used as templates for PCR. The expression levels of PEPCK, G6 Pase, and PPARα mRNA were measured and quantified by image analysis, and values were normalized to GAPDH mRNA expression.

Hepatic Targeted Gene Expressions:

As shown in FIGS. 4A, 4B and 4C, the STZ induced higher mRNA levels of PEPCK, G6 Pase, sterol regulatory element binding protein 1c (SREBP1c), and DGAT2, whereas PPARα and carnitine palmitoyl transferase Ia (CPT1a) expressions were lower in the STZ group than in the CON group. Treatment with TT1, TT2, TT3, Metf, or Feno showed decreased mRNA levels of PEPCK, G6 Pase, SREBP1c, and DGAT2 relative to those in the CON group. Treatment with TT1, TT2, TT3, Metf, or Feno increased the mRNA level of PPARα.

Figure 5A:
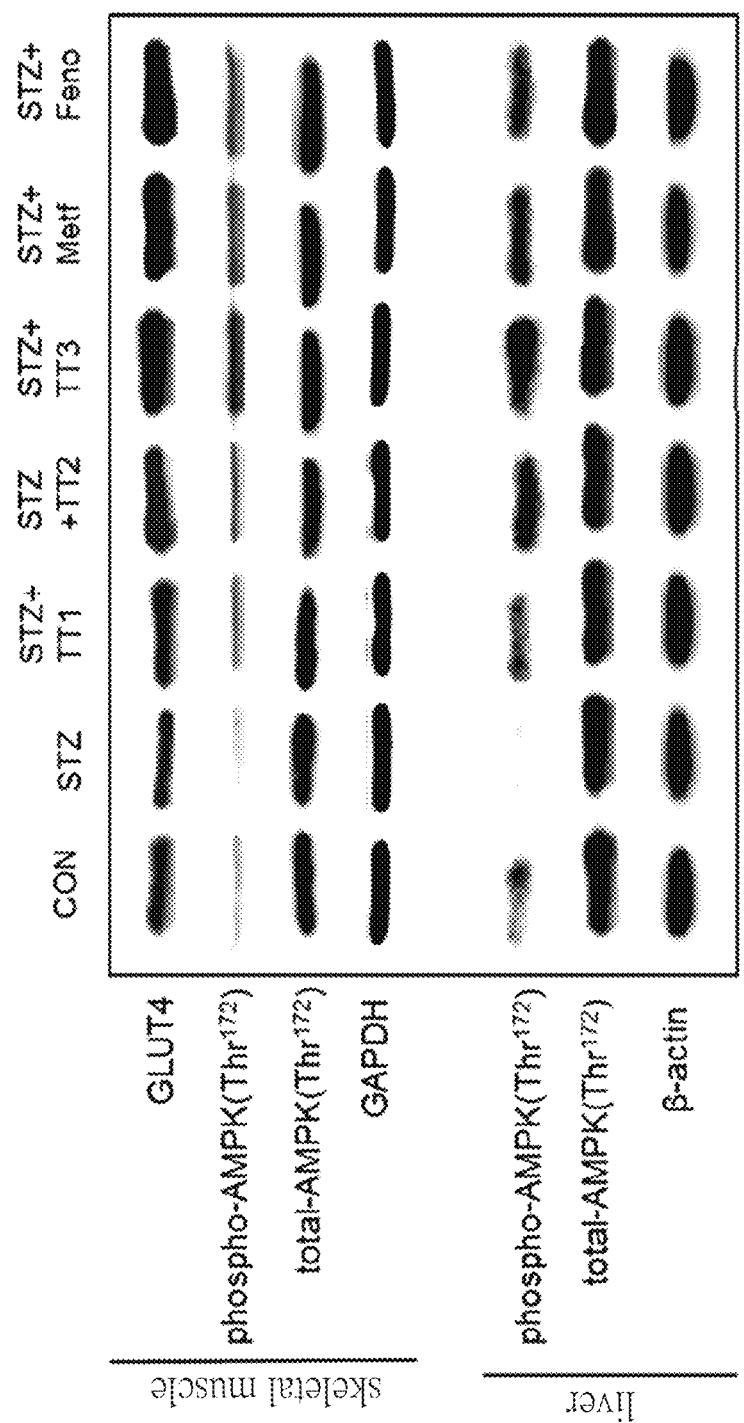
FIG. 5A is a representative image showing phospho-AMPK (Thr$^{172}$) protein contents in liver and skeletal muscle and GLUT4 protein contents in skeletal muscle of the mice by oral gavage dehydroeburicoic acid (TT), protein was separated by 12% SDS-PAGE detected by Western blot. (#) P<0.05, (##) P<0.01, and (###) P<0.001 compared with the control (CON) group; (*) P<0.05, (* *) P<0.01, and (* * *) P<0.001 compared with the streptozotocin plus vehicle (distilled water) (STZ) group. TT1, TT2, and TT3, dehydroeburicoic acid (TT1, TT2, TT3, 10, 20, and 40 mg/kg body weight, respectively); metformin (Metf) group (300 mg/kg body weight); or fenofibrate (Feno) group (250 mg/kg body weight)
Figure 5B:
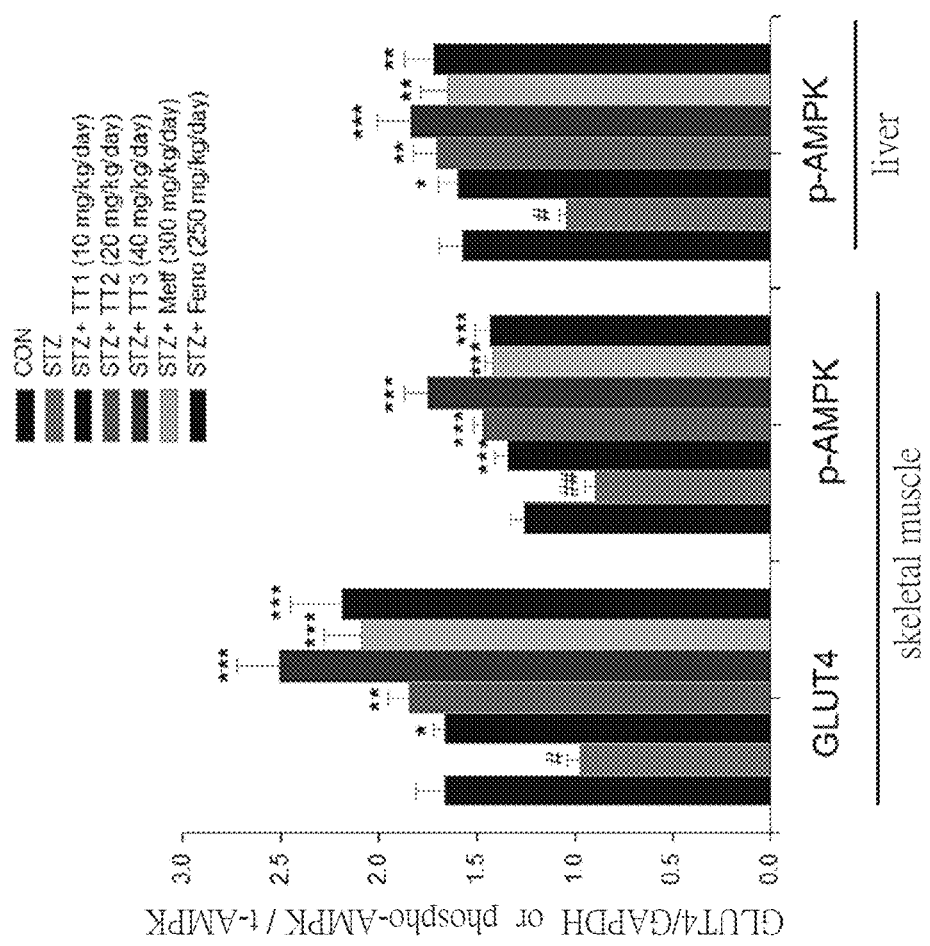
FIG. 5B shows the quantification of the GLUT4 expression levels and the ratio of phospho-AMPK to total AMPK (mean±SE, n=9)
Figure 6A:
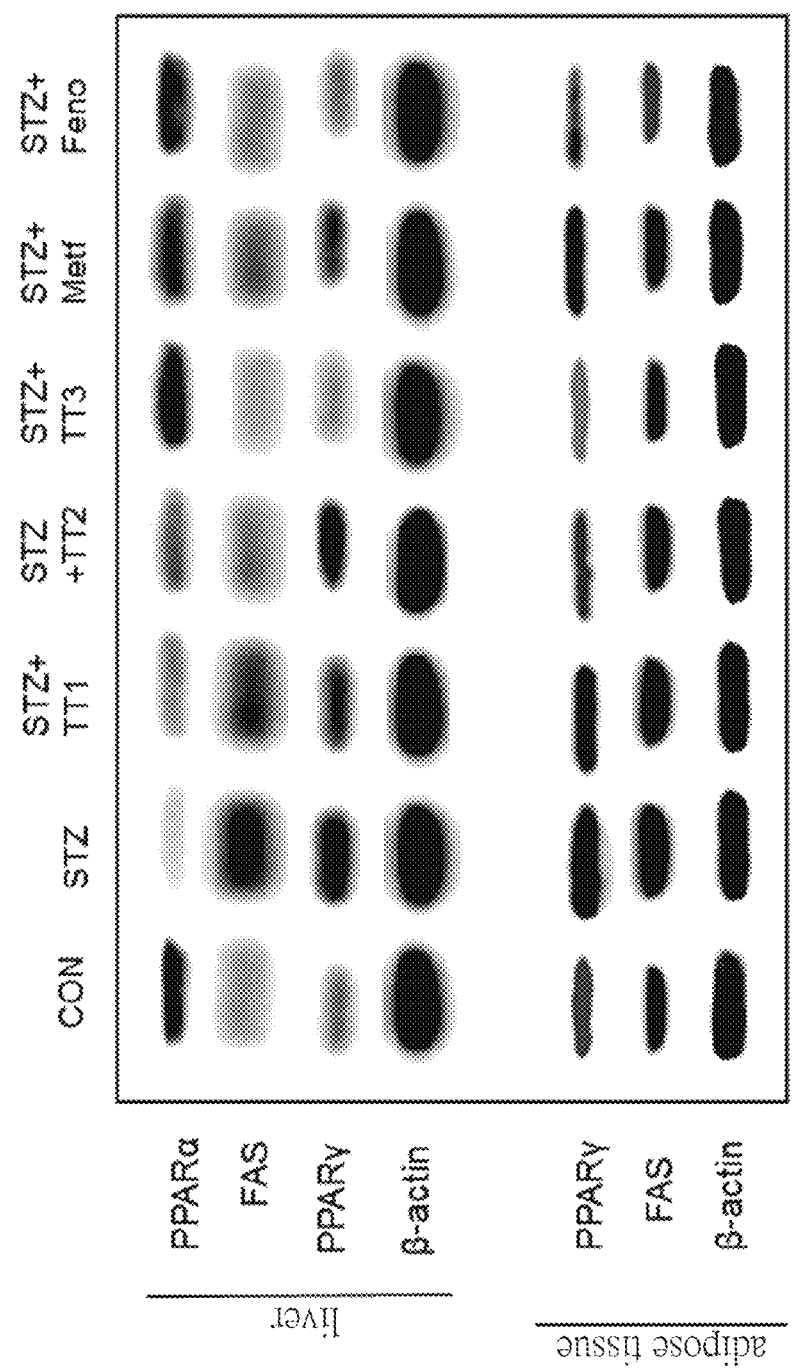
FIG. 6A is a representative image showing expression levels of PPARα, FAS, and PPARγ in the liver and of FAS and PPARγ in adipose tissue of mice by oral gavage dehydroeburicoic acid (TT), protein was separated by 12% SDS-PAGE detected by Western blot. All values are means±SE (n=9). (#) P<0.05, (##) P<0.01, and (###) P<0.001 compared with the control (CON) group, (*) P<0.05, (* *) P<0.01, and (* * *) P<0.001 compared with the streptozotocin plus vehicle (distilled water) (STZ) group. TT1, TT2, and TT3, dehydroeburicoic acid (TT1, TT2, TT3, 10, 20, and 40 mg/kg body weight, respectively); metformin (Metf) group (300 mg/kg body weight); or fenofibrate (Feno) group (250 mg/kg body weight)
Figure 6C:
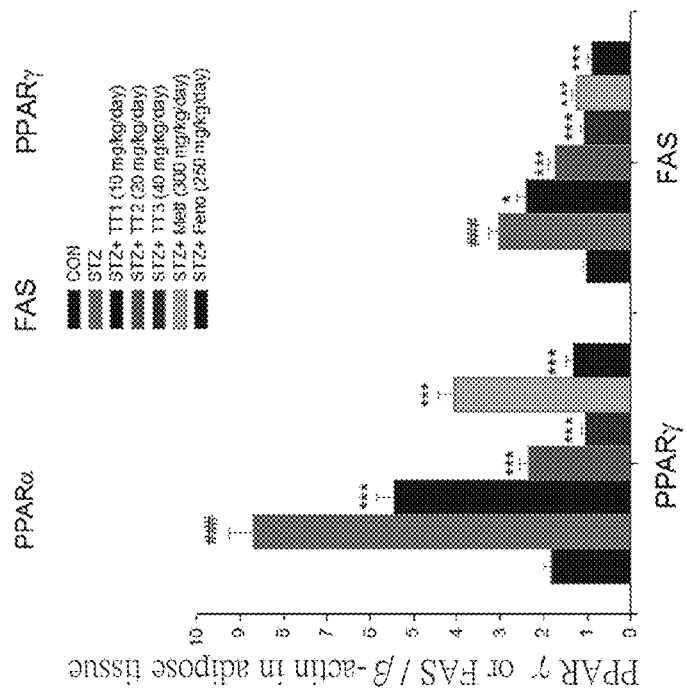
FIG. 6C illustrates expression levels of FAS and PPARγ in adipose tissue.
Figure 6B:
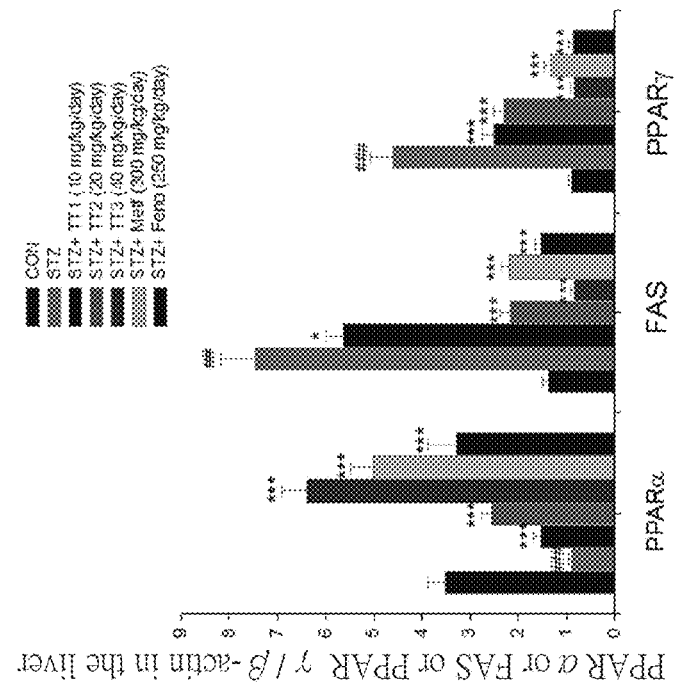
FIG. 6B illustrates the quantification of the expression levels of PPARα, FAS, and PPARγ in the liver.

Targeted Gene Expression Levels in Different Tissues:

As shown in FIGS. 5A and 5B, at the end, the membrane expressions levels of GLUT4 were lower in the STZ group than in the CON group in skeletal muscle (P<0.05). The expression levels of GLUT4 were greater in TT1-, TT2-, TT3-, Metf-, and Feno-treated groups than in the STZ group (P<0.05, P<0.01, P<0.001, P<0.001, and P<0.001, respectively). At the end of the experiment, the expression levels of phospho-AMPK/total AMPK were lower in the STZ group than in the CON group in skeletal muscle and liver (P<0.01 and P<0.05, respectively). After the treatment, the expression levels of phospho-AMPK/total AMPK were increased in skeletal muscle in the TT1-, TT2-, TT3-, Metf-, and Feno-treated groups (P<0.001, P<0.001, P<0.001, P<0.001, and P<0.001, respectively). Following the treatment, the muscular expression levels of phospho-AMPK/total AMPK were increased in the TT1-, TT2-, TT3-, Metf-, and Feno-treated groups compared with the STZ group (P<0.05, P<0.01, P<0.001, P<0.01, and P<0.01, respectively) (FIG. 5).

As shown in FIGS. 6A and 6B, at the end, the expression levels of PPARα were lower in the STZ group than in the CON group in the liver (P<0.001). After the treatment, the expression levels of PPARα were increased in the liver in the TT1-, TT2-, TT3-, Metf-, and Feno-treated groups (P<0.001, P<0.001, P<0.001, P<0.001, and P<0.001, respectively). The expression levels of FAS and PPARγ were higher in the STZ group than in the CON group in the liver (P<0.01 and P<0.001, respectively). After the treatment, the expression levels of FAS and PPAR γ were decreased in the liver in the TT1-, TT2-, TT3-, Metf-, and Feno-treated groups. The expression levels of PPARγ and FAS were higher in the STZ group than in the CON group in adipose tissue (P<0.001 and P<0.001, respectively). After the treatment, the expression levels of PPARγ and FAS were decreased in adipose tissue in the TT1-, TT2-, TT3-, Metf-, and Feno-treated groups.

In conclusion, the present invention explored the effects of dehydroeburicoic acid (TT) in the treatment of diabetes and dyslipidemia. TT not only significantly lowered blood glucose levels but also reduced the levels of blood triglyceride and total cholesterol. TT markedly increased membrane GLUT4 protein levels in membrane of skeletal muscle to elevate glucose uptake. Moreover, TT increased the expression levels of phospho-AMPK/total AMPK in both skeletal muscle and liver tissue. TT decreased mRNA levels of PEPCK and G6 Pase, which was related to the inhibition of hepatic glucose production. The combination of enhanced membrane GLUT4 in skeletal muscle and decreased glucose production in the liver leads to lower blood glucose levels. TT decreased plasma triglycerides, hepatic steatosis, and total cholesterol levels through inhibition of hepatic FAS and PPARγ accompanied by reduced SREBP1c and DGAT2 mRNA levels, whereas increased expression levels of PPARα accompanied by enhanced CPT1a mRNA levels increase fatty acids oxidation in the liver. TT treatment decreased lipogenic genes including PPARγ and FAS in adipose tissue, which may contribute to decreasing adipose cell differentiation and lipid storage. Furthermore, TT decreased SREBP2 mRNA levels, thus leading to a decrease in blood total cholesterol levels. Our findings imply that TT has an excellent therapeutic potential in the treatment of type 1 diabetes associated with hyperlipidemia.

The first object of the present invention provides a component, dehydroeburicoic acid (TT), from mycelium of Antrodia camphorata extract to treat diabetes. Accordingly, the present invention provides a new use of dehydroeburicoic acid (TT), which administrated to a subject with type 1 diabetes mellitus and hyperlipidemia has following effects.

A primary objective of the present invention is to provide a method for treating type 1 diabetes, hyperlipidemia or hepatic ballooning degeneration, comprising administering to a subject in need thereof an effective amount of compounds represented by formula (I).

Another objective of the present invention is to provide a method for decreasing mRNA levels of phosphoenol pyruvate carboxykinase (PEPCK), glucose-6-phosphatase (G6 Pase), sterol regulatory element binding protein 1c (SREBP1c), diacylglycerol acyltransferase 2 (DGAT2), and SREBP2, but increasing mRNA levels of peroxisome proliferator activated receptor α (PPARα) and CPT1a in a cell, comprising contacting the cell with an effective amount of compound.

Another objective of the present invention is to provide a method for increasing expression levels of membrane glucose transporter 4 (GLUT4) in skeletal muscle and phospho-AMPK in both skeletal muscle and liver tissue, comprising contacting the tissue with an effective amount of compounds represented by formula (I)

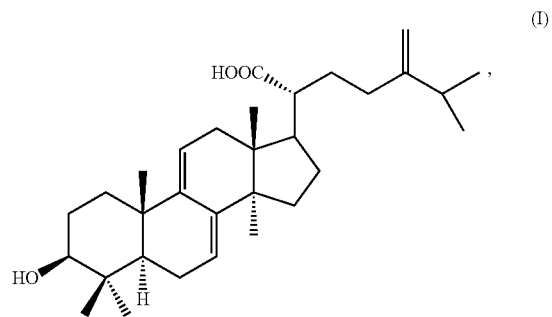

According to an embodiment of the present invention, the compounds are obtained from *Antrodia camphorata*, and the compound is dehydroeburicoic acid (TT).

According to an embodiment of the present invention, the effective amount of the compounds given is from 10 mg/kg to 40 mg/kg per day.

According to an embodiment of the present invention, the cell or tissue is obtained from a subject with type 1 diabetes mellitus.

According to an embodiment of the present invention, the compounds treat diabetes by decreasing blood glucose levels, and increasing insulin concentration.

According to an embodiment of the present invention, the cell or tissue is obtained from a subject with a condition of hyperlipidemia, hypertriglyceridemia, hypercholesterolemia.

According to an embodiment of the present invention, the compound treat hepatic ballooning degeneration induced by streptozotocin (STZ) to reduce hepatic ballooning degeneration.

According to an embodiment of the present invention, the compound treat hyperleptinemia induced by streptozotocin (STZ) to reduce blood leptin levels.

The present invention provides a method for treating diabetes, hyperlipidemia or hepatic total lipids by using dehydroeburicoic acid (TT), this compound can significantly lower the blood markers, such as blood glucose, total cholesterol (TC), triglyceride (TG), insulin, and leptin levels in subjects with type 1 diabetes, hyperlipidemia or hepatic ballooning degeneration. Therefore, the method of the present invention provides a new strategy to prevent and treat type 1 diabetes mellitus, hypertriglyceridemia or hypercholesterolemia.

According to an embodiment of the present invention, this compound treats hyperglycemia by enhancing membrane GLUT4 in skeletal muscle, and increasing phospho-AMPK protein expression in skeletal muscle and liver, but decreasing mRNA levels of PEPCK and G6 Pase, thus lowering blood glucose levels.

According to an embodiment of the present invention, this compound treats hypertriglyceridemia, and hepatic steatosis through inhibition of hepatic fatty acid synthase (FAS) and peroxisome proliferator activated receptor γ (PPARγ) accompanied by reduced sterol response element binding protein-1c (SREBP1c) and diacyl glycerol acyltransferase 2 (DGAT2) mRNA levels, but increases expression levels of peroxisome proliferator activated receptor α (PPARα) accompanied by enhanced carnitine palmitoyltransferase-1a (CPT1a) mRNA levels increase fatty acids oxidation in the liver.

According to an embodiment of the present invention, this compound treats hypercholesterolemia by decreasing SREBP2 mRNA levels, thus leading to a decrease in blood total cholesterol (TC) levels.

According to an embodiment of the present invention, this compound treats hepatic steatosis and reduce ballooning of hepatocyte, by decreasing adipose and hepatic lipogenic genes expression of PPARγ and FAS, but increasing PPARα, which may contribute to decreasing lipid accumulation both in adipose and liver tissue.

While we have shown and described various embodiments in accordance with the present invention, it is clear to those skilled in the art that further embodiments may be made without departing from the scope of the present invention.

What is claimed is:

1. A method for treating hyperglycemia or hyperlipidemia, comprising administering to a subject suffering from type 1 diabetes an effective amount of a compound represented by formula (I):

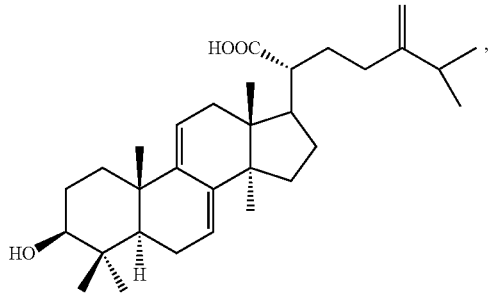

wherein the effective amount of the compound is in a range from 10 mg/kg to 40 mg/kg per day.

2. The method according to claim 1, wherein the compound is obtained from mycelium of *Antrodia camphorata*.

3. The method according to claim 1, wherein the compound decreases blood glucose level or increases insulin concentration.

4. The method according to claim 1, wherein the compound decreases plasma triglycerides and total cholesterol level.

5. The method according to claim 1, wherein the compound reduces blood leptin level.

6. The method according to claim 1, wherein the compound increases expression level of phospho-Akt.

7. The method according to claim 1, wherein the hyperlipidemia is hypertriglyceridemia, hypercholesterolemia, or a combination thereof.

8. The method according to claim 1, wherein the compound treats hyperglycemia by increasing expression levels of membrane GLUT4 in skeletal muscle and phospho-AMPK in skeletal muscle and liver, but decreasing mRNA level of PEPCK and G6Pase.

9. The method according to claim 1, wherein the compound treats hypertriglyceridemia by inhibiting hepatic fatty acid synthase (FAS) and peroxisome proliferator activated receptor γ (PPARγ) and reducing mRNA levels of sterol regulatory element binding protein 1c (SREBP1c) and diacylglycerol acyltransferase 2 (DGAT2), but increasing expression levels of peroxisome proliferator activated receptor α (PPARα) and mRNA levels of CPT1a.

10. A method for treating type 1 diabetes, comprising administering to a subject in need thereof an effective amount of a compound represented by formula (I):

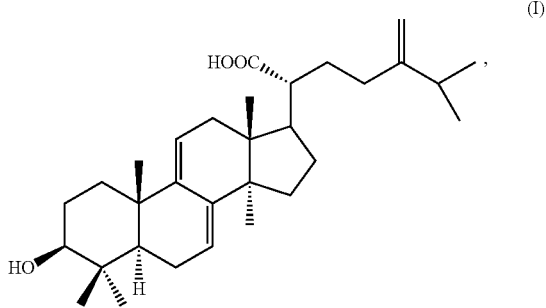

wherein the effective amount of the compound is in a range from 10 mg/kg to 40 mg/kg per day.

* * * * *